(12) United States Patent
Song (10) Patent No.: US 11,914,216 B2
(45) Date of Patent: Feb. 27, 2024

(54) INTEGRATED OPTICAL ENGINE HAVING CAMERA

(71) Applicant: CLAROPTIC CO., Ltd., Seongnam-si (KR)

(72) Inventor: Min-kyu Song, Seoul (KR)

(73) Assignee: CLAROPTIC CO., Ltd., Seongnam-si (KR)

( * ) Notice: Subject to any disclaimer, the term of this patent is extended or adjusted under 35 U.S.C. 154(b) by 0 days.

(21) Appl. No.: 18/122,685

(22) Filed: Mar. 16, 2023

(65) Prior Publication Data

US 2023/0358991 A1    Nov. 9, 2023

(30) Foreign Application Priority Data

May 6, 2022   (KR) .......................... 10-2022-0056151

(51) Int. Cl.
| | |
|---|---|
| *G02B 7/02* | (2021.01) |
| *H04N 9/31* | (2006.01) |
| *G02B 7/182* | (2021.01) |
| *G03B 17/54* | (2021.01) |

(Continued)

(52) U.S. Cl.
CPC ............. *G02B 7/021* (2013.01); *G02B 7/182* (2013.01); *H04N 9/3141* (2013.01)

(58) Field of Classification Search
CPC ............. H04N 1/02481; H04N 1/0249; H04N 5/7491; H04N 23/54; H04N 23/55; H04N 2201/02404; H04N 2201/02452; H04N 2201/02406; H04N 2201/03154; H04N 2201/02479; H04N 2201/0448; G02B 7/02; G02B 7/021; G02B 7/022; G02B 7/023; G02B 7/025; G02B 7/026; G02B 7/027; G02B 7/028

See application file for complete search history.

(56) References Cited

U.S. PATENT DOCUMENTS

| | | | |
|---|---|---|---|
| 2002/0126399 A1* | 9/2002 | Takanashi | G02B 26/0875 359/822 |
| 2011/0157903 A1* | 6/2011 | Trewin | F21V 23/06 362/418 |

(Continued)

FOREIGN PATENT DOCUMENTS

| | | |
|---|---|---|
| JP | 2006-234920 A | 9/2006 |
| JP | 2017-533000 A | 11/2017 |
| KR | 10-2337757 B1 | 12/2021 |

*Primary Examiner* — Ephrem Z Mebrahtu
(74) *Attorney, Agent, or Firm* — Park, Kim & Suh, LLC (57) ABSTRACT

An integrated optical engine based on an embodiment of the invention includes: a projecting system for projecting light to the exterior; an imaging system for receiving light from the exterior; a camera body, to which the projecting system and the imaging system are coupled; and a base coupled to the rear of the camera body. A first insertion recess extends along the lengthwise direction of the camera body and has the same diameter as the outer diameter of the projecting system such that the projecting system is movable within the first insertion recess along only the lengthwise direction, and a second insertion recess extends along the lengthwise direction of the camera body and has the same diameter as the outer diameter of the imaging system such that the imaging system is movable within the second insertion recess along only the lengthwise direction.

8 Claims, 8 Drawing Sheets

(51) Int. Cl.
  *G03B 17/12* (2021.01)
  *G03B 17/55* (2021.01)

(56) References Cited

U.S. PATENT DOCUMENTS

2016/0330355 A1* 11/2016 Tchouprakov ......... H04N 25/71
2020/0170497 A1* 6/2020 Chang ................... H04N 23/55

* cited by examiner

INTEGRATED OPTICAL ENGINE HAVING CAMERA

CROSS-REFERENCE TO RELATED APPLICATIONS

This application claims the benefit of Korean Patent Application No. 10-2022-0056151, filed with the Korean Intellectual Property Office on May 6, 2022, the disclosure of which is incorporated herein by reference in its entirety.

BACKGROUND

1. Technical Field

The present invention relates to an integrated optical engine having a camera.

2. Description of the Related Art

An optical projector is a device that uses optical lenses to project a small image onto a large screen, where the mechanism of the optical projector for projecting the image is referred to as an optical engine. An optical engine may be provided with a light source, such as LEDs, and lenses for refracting and reflecting the light emitted from the light source. In recent times, the optical engine is mounted with a camera (image sensor) for use as a three-dimensional scanner. An optical engine mounted with a camera as a three-dimensional scanner that is utilized as an intraoral scanner is disclosed in Korean Registered Patent No. 2337757.

The intraoral scanner disclosed in the document mentioned above includes a main body within a case, where a light projector, which corresponds to a light source, and a camera lens, through which light reflected off the external object being scanned passes, are coupled to the main body. The light that passes through the camera lens arrives at an imaging board, which is also coupled to the main body.

In the intraoral scanner disclosed in the above document, the camera lens and the light projector are each coupled to the main body, and a high level of coupling precision is required. In particular, the camera lens and the light projector, after being coupled to the main body, must undergo precise position adjustment, i.e., an alignment process. However, the structure of the conventional intraoral scanner has the camera lens and the light projector coupled separately onto the exterior of the main body. That is, the camera lens is coupled to the front of the main body, while the light projector is coupled to the rear of the main body, independent of the camera lens. Thus, with the conventional intraoral scanner, it may be very difficult to align the camera lens with the light projector, and even after these are coupled, there is a risk of the precision being decreased when an external impact, etc., is applied.

SUMMARY OF THE INVENTION

An aspect of the present invention, which was conceived to resolve the problem described above, is to provide an integrated optical engine that allows easy coupling and alignment of the projecting system and imaging system.

Other objectives of the present invention will be more clearly understood from the embodiments set forth below.

An aspect of the invention provides an integrated optical engine that includes: a projecting system, which includes multiple lenses for projecting light to the exterior; an imaging system, which includes multiple lenses for receiving light from the exterior; a camera body, to which the projecting system and the imaging system are coupled; and a base, within which a light source is coupled, and which is formed from a material having a heat-emitting capability and is coupled to the rear of the camera body. A first insertion recess, into which the projecting system may be inserted, and a second insertion recess, into which the imaging system may be inserted, are formed in the camera body, where the first insertion recess extends along the lengthwise direction of the camera body and has the same diameter as the outer diameter of the projecting system such that the projecting system is movable within the first insertion recess along only the lengthwise direction of the camera body, and the second insertion recess extends along the lengthwise direction of the camera body and has the same diameter as the outer diameter of the imaging system such that the imaging system is movable within the second insertion recess along only the lengthwise direction of the camera body. A first slot is formed in a lengthwise direction in the first insertion recess, and a second slot is formed in a lengthwise direction in the second insertion recess.

An integrated optical engine according to an embodiment of the present invention can include one or more of the following features. For example, the projecting system inserted in the first insertion recess and the imaging system inserted in the second insertion recess can remain unexposed at the exterior of the camera body.

The integrated optical engine cam further include a mirror for reflecting light that has entered the imaging system and a sensor board for receiving the light that is reflected by the mirror.

The camera body can include a sensor-coupling face, which is separated from the base and to an exposed surface of which the sensor board may be coupled, and a body opening can be formed in the sensor-coupling face to permit the transmission of light that is reflected by the mirror. Also, the camera body can include a mirror-coupling face to which the mirror may be coupled, where a filling indentation can be formed at an end portion of the mirror-coupling face.

The camera body can include a mirror-coupling space in which the mirror may be positioned, where one side of the mirror-coupling space can be open, and the mirror-coupling space can be positioned between the sensor-coupling face and the base.

A securing member can be coupled to each of the first slot and the second slot to secure the positions of the imaging system and the projecting system with respect to the lengthwise direction of the camera body.

A securing indentation, to which the securing member may be coupled, can be formed in a side of each of the projecting system and the imaging system.

The first insertion recess and the second insertion recess can be in communication with each other through a rectangular connection hole.

An embodiment of the present invention having the features above can provide various advantageous effects including the following. However, an embodiment of the present invention may not necessarily exhibit all of the effects below.

An embodiment of the present invention can provide an integrated optical engine that allows easy coupling and alignment of the projecting system and imaging system.

DETAILED DESCRIPTION OF THE INVENTION

As the invention allows for various changes and numerous embodiments, particular embodiments will be illustrated in the drawings and described in detail in the written description. However, this is not intended to limit the present invention to particular modes of practice, and it is to be appreciated that all changes, equivalents, and substitutes that do not depart from the spirit and technical scope of the present invention are encompassed by the present invention. In the description of the present invention, certain detailed explanations of the related art are omitted if it is deemed that they may unnecessarily obscure the essence of the invention.

The terms used in the present specification are merely used to describe particular embodiments and are not intended to limit the present invention. An expression used in the singular encompasses the expression of the plural, unless it has a clearly different meaning in the context. In the present specification, it is to be understood that terms such as "including" or "having," etc., are intended to indicate the existence of the features, numbers, steps, actions, components, parts, or combinations thereof disclosed in the specification and are not intended to preclude the possibility that one or more other features, numbers, steps, actions, components, parts, or combinations thereof may exist or may be added.

While such terms as "first" and "second," etc., can be used to describe various components, such components are not to be limited by the above terms. The above terms are used only to distinguish one component from another.

Certain embodiments of the present invention will be described below in more detail with reference to the accompanying drawings. Those components that are the same or are in correspondence are rendered the same reference numeral, and redundant descriptions are omitted.

Figure 1:
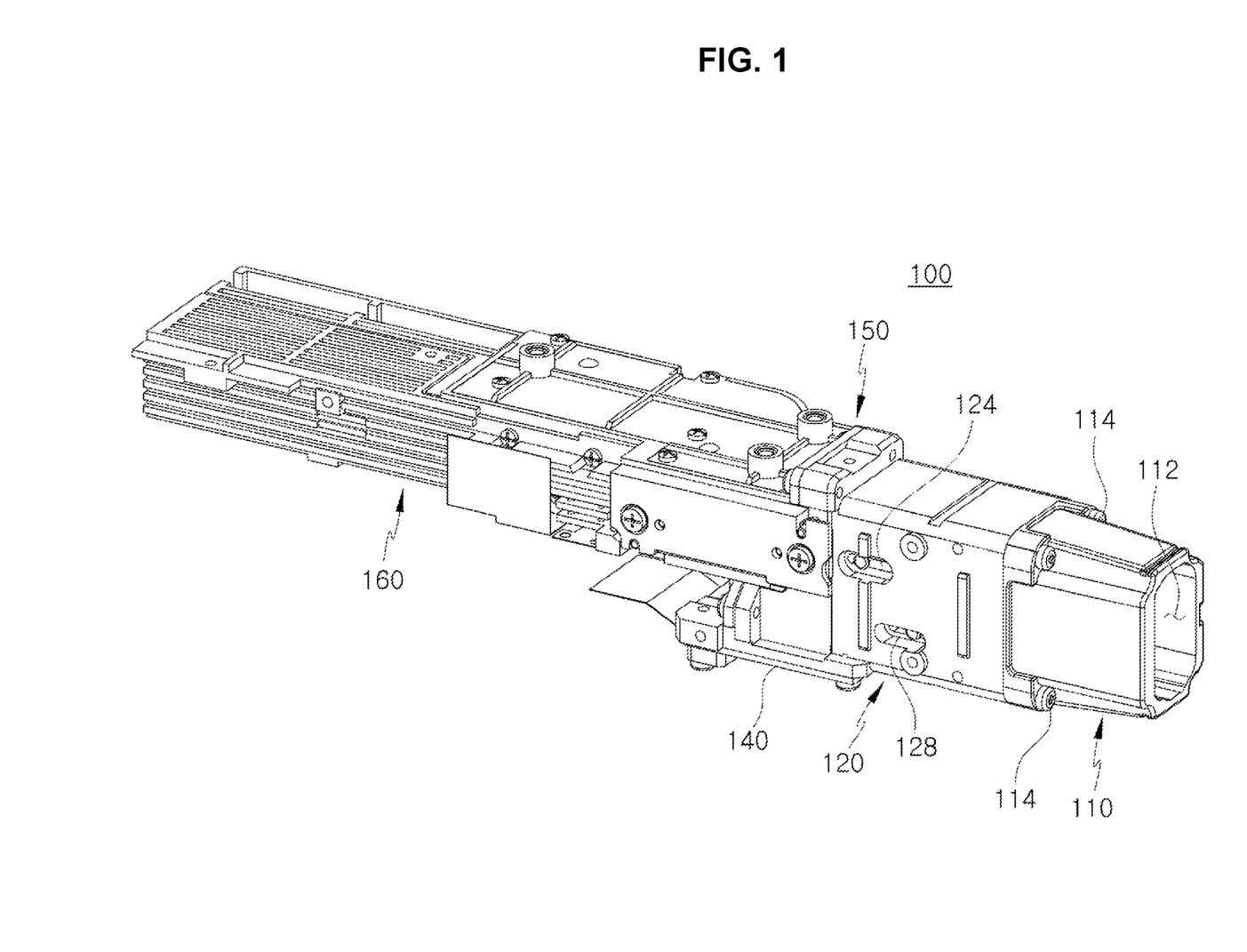
FIG. 1 and FIG. 2 are perspective views illustrating an integrated optical engine according to an embodiment of the invention.
Figure 2:
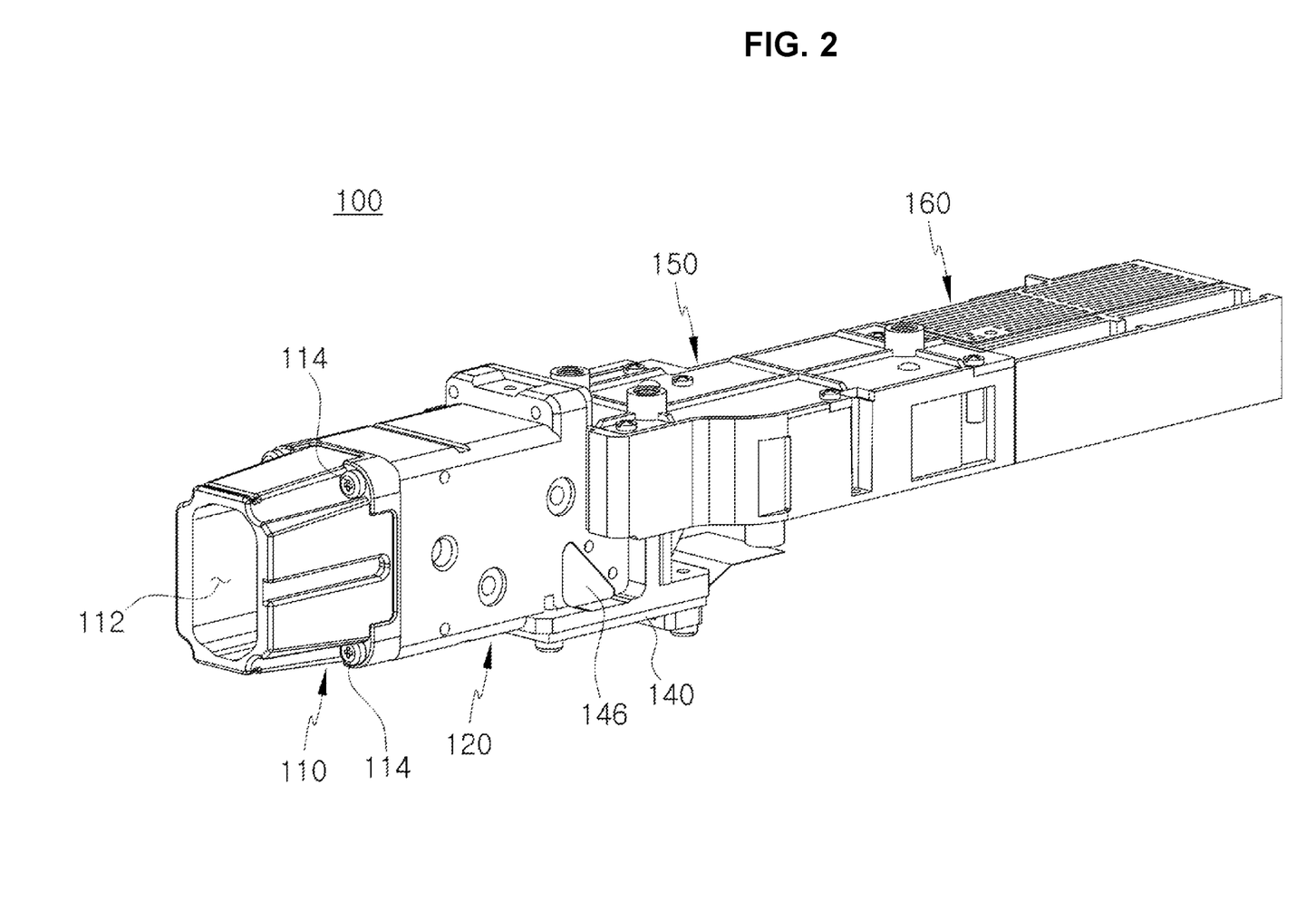
Figure 3:
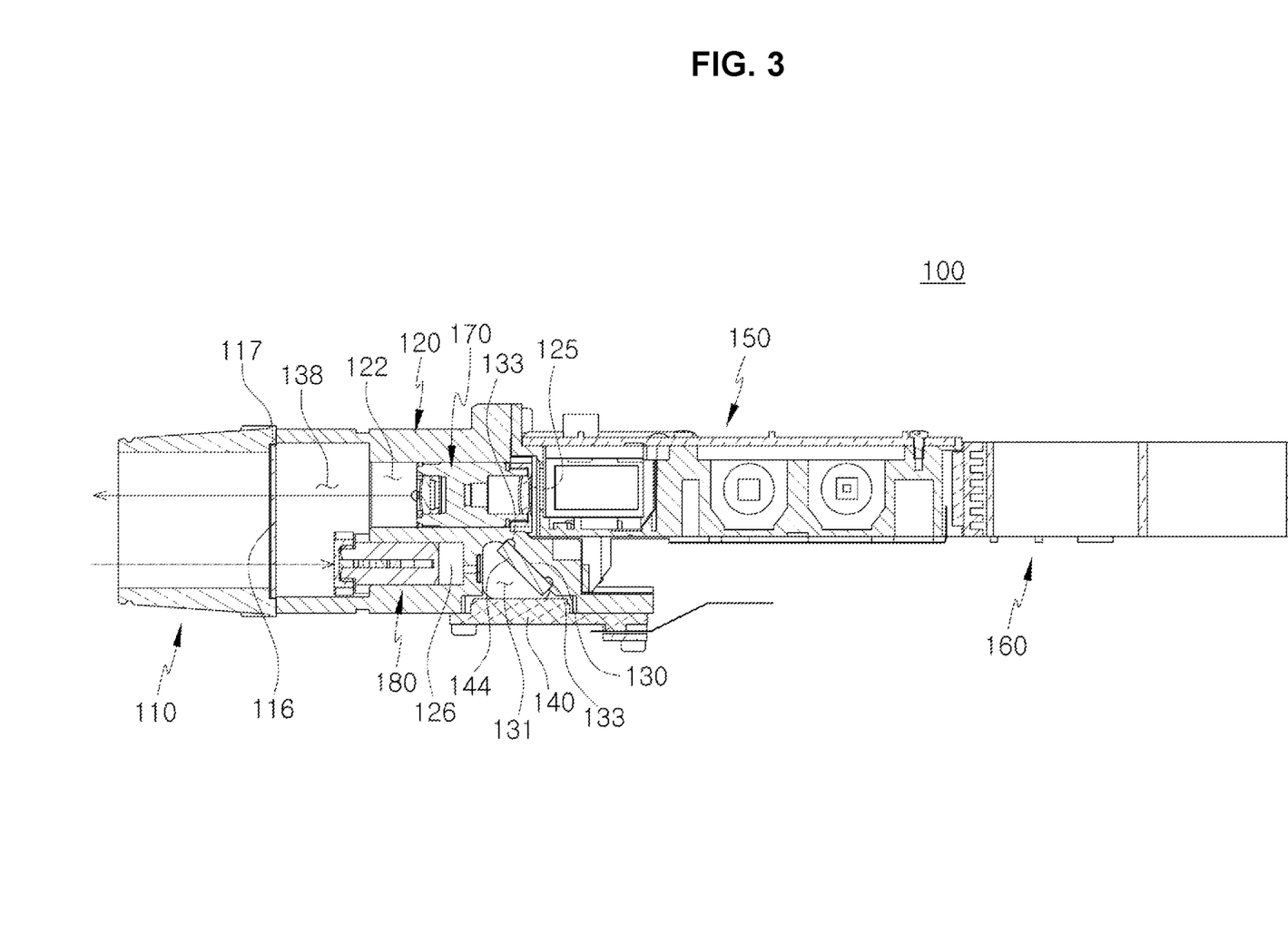
FIG. 3 is a cross-sectional view of the integrated optical engine illustrated in FIG. 1 showing the projecting system and the imaging system coupled on the inside.
Figure 4:
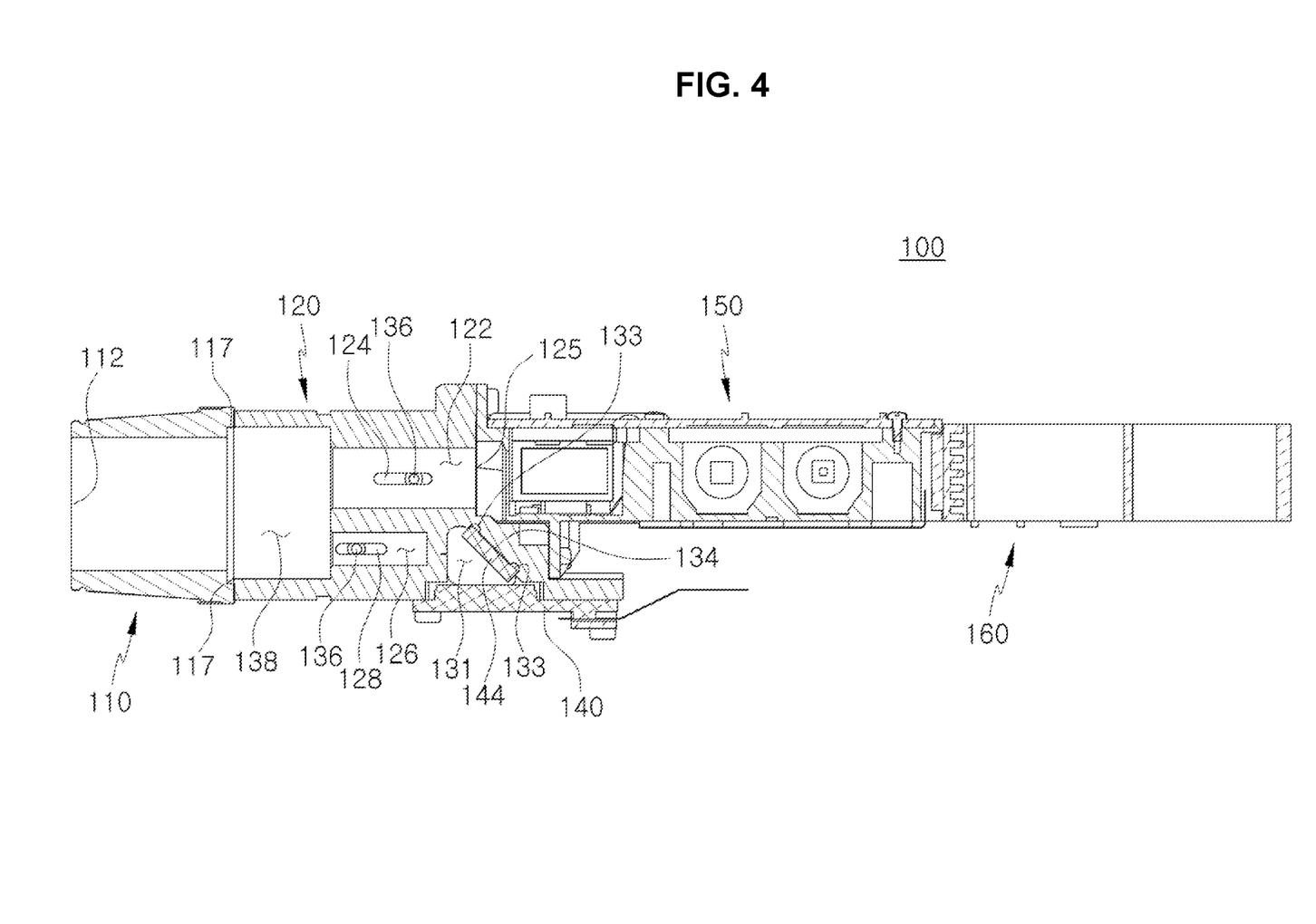
FIG. 4 is a cross-sectional view of the integrated optical engine illustrated in FIG. 3 with the projecting system and the imaging system removed.
Figure 5:
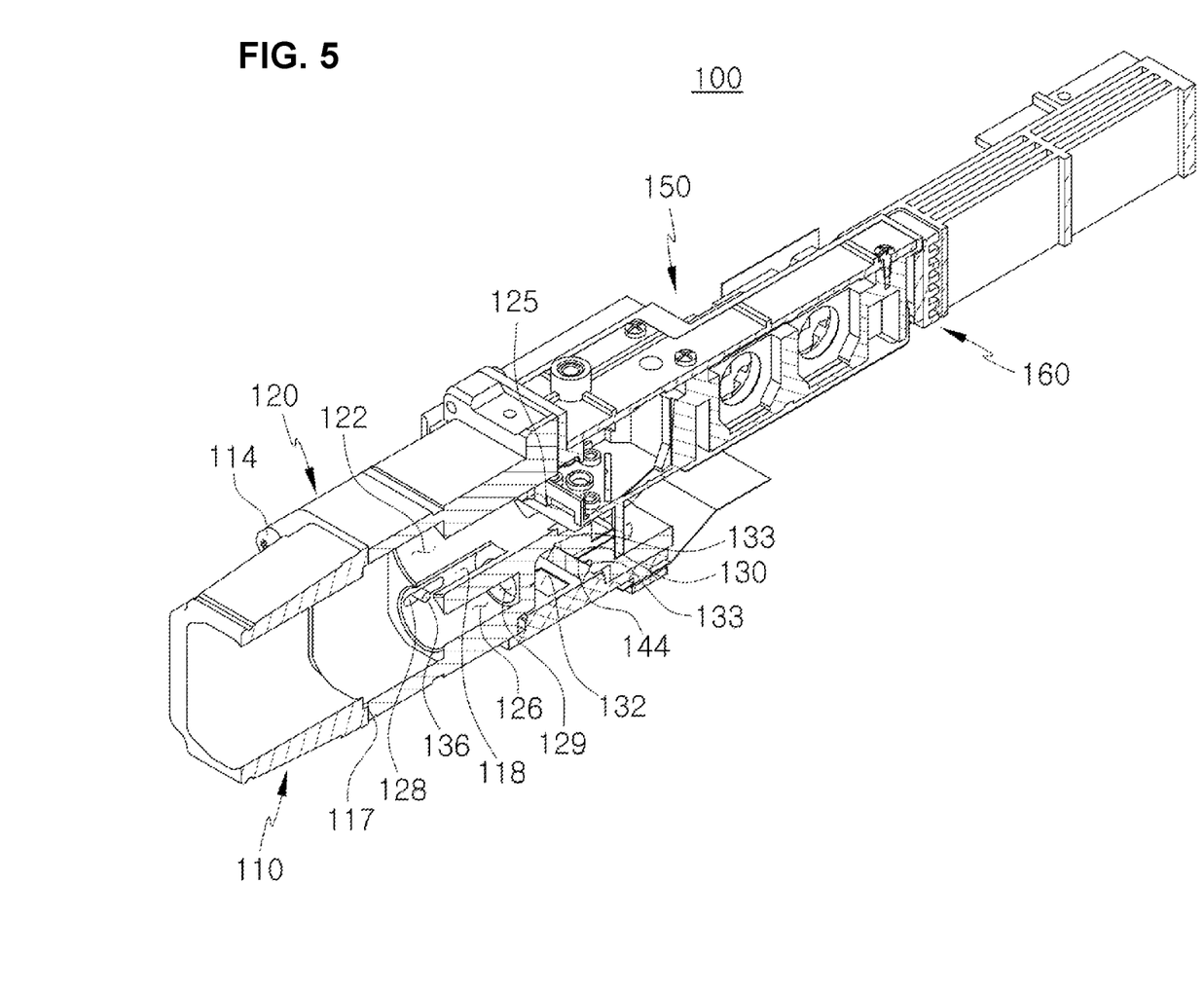
FIG. 5 is a perspective cross-sectional view of the integrated optical engine illustrated in FIG. 1 with the projecting system and the imaging system removed.

FIG. 1 and FIG. 2 are perspective views illustrating an integrated optical engine 100 according to an embodiment of the invention. FIG. 3 and FIG. 4 are cross-sectional views of the integrated optical engine 100 illustrated in FIG. 1, and FIG. 5 is a perspective cross-sectional view. FIG. 3 illustrates the optical engine 100 with the projecting system 170 and the imaging system 180 coupled on the inside, while FIG. 4 and FIG. 5 illustrate the optical engine 100 with the projecting system 170 and the imaging system 180 removed.

Referring to FIGS. 1 to 5, an integrated optical engine 100 according to an embodiment of the invention may be coupled within the case of an intraoral scanner (not shown), etc., to emit light for scanning and generate an image from the reflected light. To this end, a light source (not shown) and a projecting system 170 as well as a sensor board 140 and an imaging system 180, which correspond to a camera, may be provided in the integrated optical engine 100. The integrated optical engine 100 may also include a probe tip mount 110, a camera body 120, a base 150, and a heat sink 160.

The probe tip mount 110 can be coupled to the front of the camera body 120 by way of coupling bolts 114, and a probe (not shown) can be coupled to the front of the probe tip mount 110. A tip opening 112 corresponding to an optical path may be formed in the probe tip mount 110. Through the tip opening 112, light from the light source may be projected to the outside, and light from the outside may enter the inside. The probe tip mount 110 can be fabricated from a heat-emitting material.

A polarizing filter 116 can be provided at the juncture between the probe tip mount 110 and the camera body 120. The polarizing filter 116 may be disposed perpendicularly to the optical path (represented by arrows) within the camera body 120. For this, a holding indentation 117 may be formed in the rear of the probe tip mount 110. The edges of the polarizing filter 116 may be held and secured in the holding indentation 117. Thus, an integrated optical engine 100 according to this embodiment uses a simple structure such as the holding indentation 117 to allow an easy coupling of the polarizing filter 116.

The emitted light that passes through the projecting system 170 and the incident light that passes through the imaging system 180 can both pass through a single polarizing filter 116. The polarizing filter 116 can be disposed perpendicularly to the front surfaces of the projecting system 170 and the imaging system 180.

The camera body 120 may be disposed between the probe tip mount 110 and the base 150, and the projecting system 170 and the imaging system 180 may be coupled within the camera body 120. A sensor board 140 corresponding to a camera may be coupled to one side of the camera body 120, and a mirror 144 may be coupled behind the imaging system 180 within the camera body 120. Thus, an integrated optical engine 100 according to this embodiment may provide the advantage of easy coupling by including a camera body 120 to which the projecting system 170, imaging system 180, and mirror 144 can be coupled.

The camera body 120 can be fabricated from a plastic resin, etc., and can be fabricated from a material having high heat resistance. Of course, the invention is not limited by the material of the camera body 120, and it is possible to fabricate the camera body 120 from various other materials such as metal, etc.

The base 150 may be coupled to the rear of the camera body 120. A light source (not shown) can be coupled within the base 150. The light emitted from the light source may enter the projecting system 170 through a first through-hole 125 of the camera body 120 and then be outputted to the exterior. Thus, the base 150 may be in communication with a first insertion recess 122 of the camera body 120.

Since the light source, which may reach high temperatures, is coupled within the base 150, the base 150 can be fabricated by a material having high heat emissivity (such as metal, etc.). The base 150 can be separably coupled by bolts (no reference numeral) or the like to the camera body 120 at its front and the heat sink 160 at its rear.

The heat sink 160 can be coupled to the rear of the base 150. The heat sink 160 can correspond to heat-emitting pins that allow the heat generated at the light source to easily be emitted to the exterior.

Figure 6:
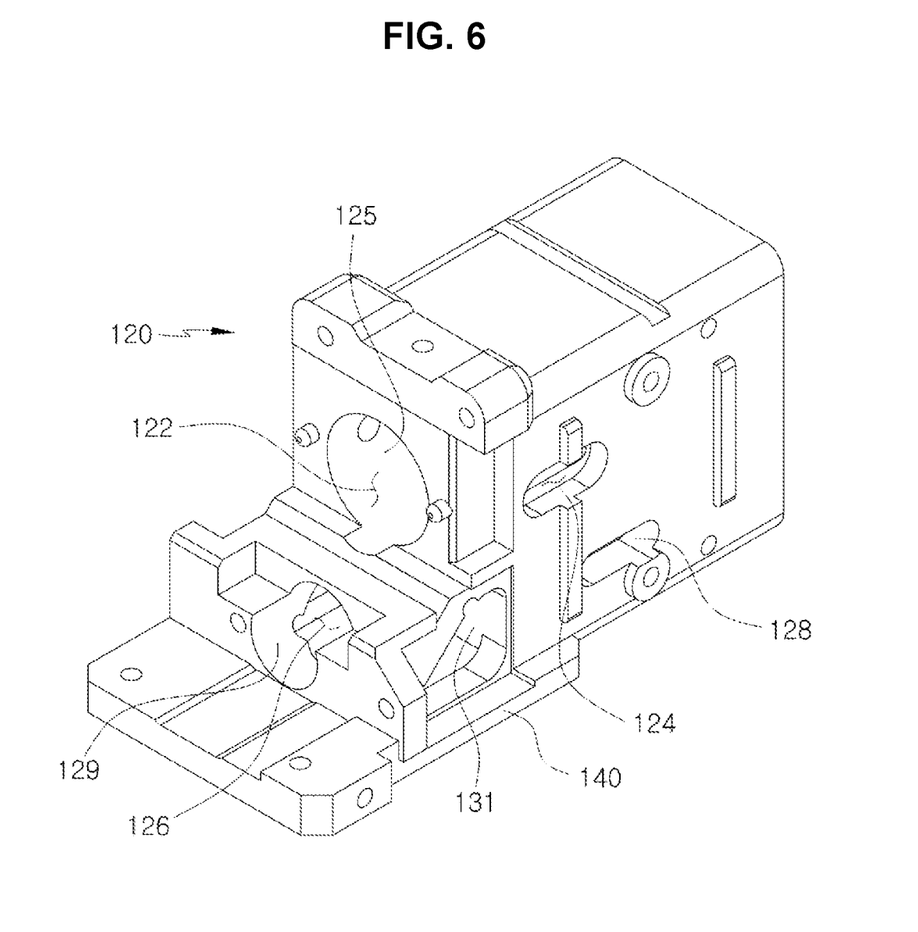
FIG. 6 and FIG. 7 are perspective views illustrating the camera body of an integrated optical engine according to an embodiment of the invention.
Figure 7:
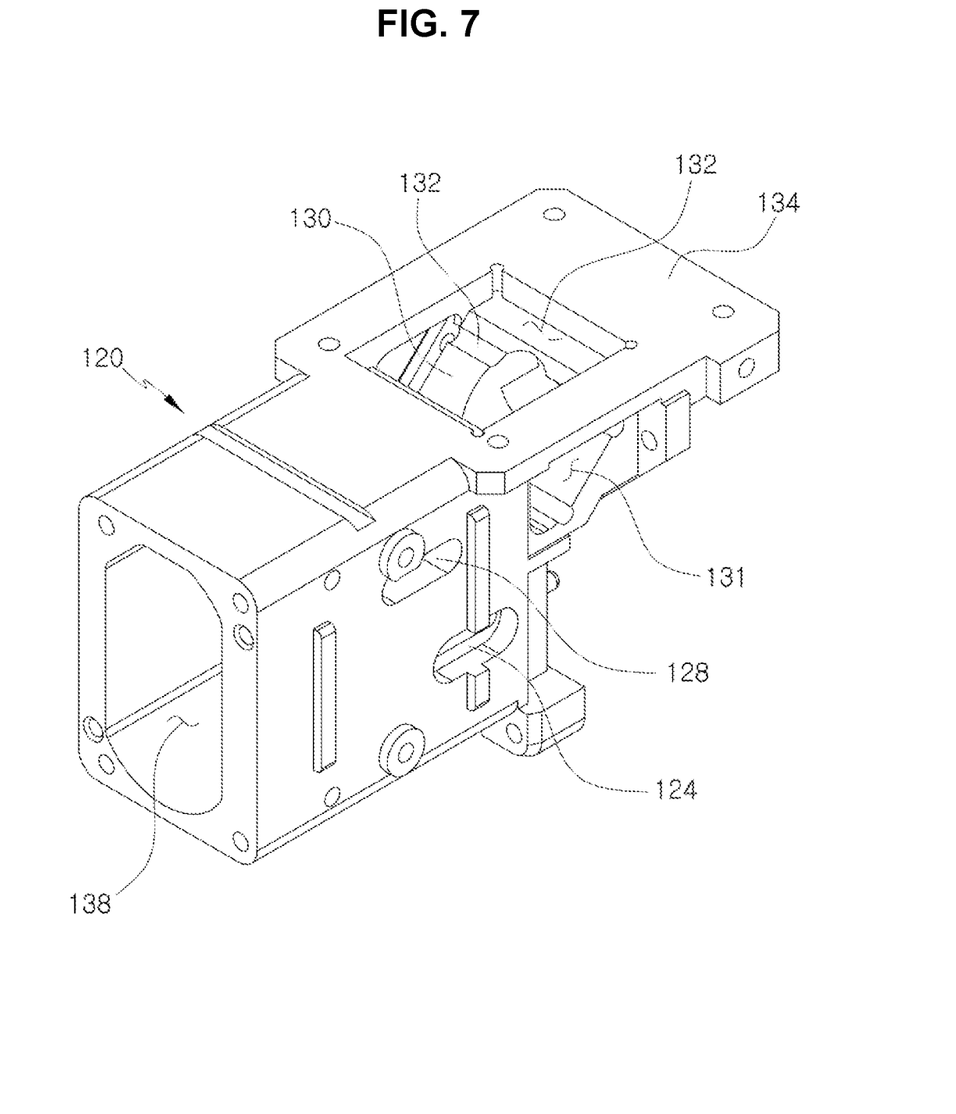
Figure 8:
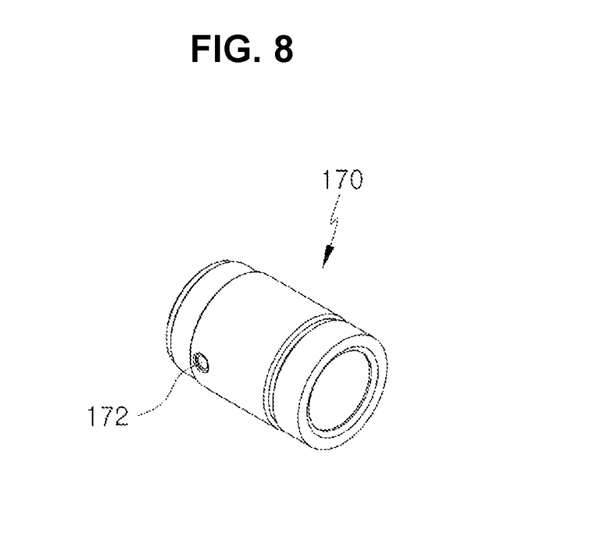
FIG. 8 is a perspective view illustrating the projecting system.
Figure 9:
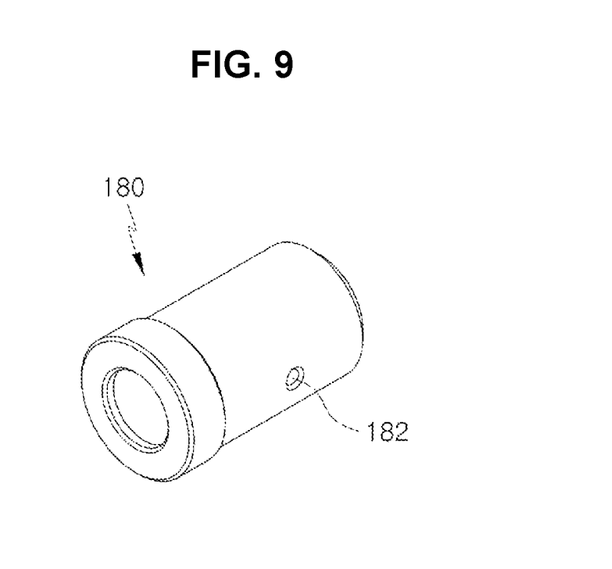
FIG. 9 is a perspective view illustrating the imaging system.

FIG. 6 and FIG. 7 are perspective views illustrating the camera body 120 of an integrated optical engine 100 according to an embodiment of the invention. Also, FIG. 8 is a perspective view illustrating the projecting system 170, and FIG. 9 is a perspective view illustrating the imaging system 180.

Referring to FIGS. 3 to 9, the camera body 120 may include an interior space, with a first insertion recess 122 and a second insertion recess 126 formed in said interior space. The projecting system 170 and imaging system 180 inserted in the first insertion recess 122 and second insertion recess 126 can remain unexposed at the exterior of the camera body 120.

The first insertion recess 122 may be a recess having a circular cross section and may extend a particular length. The first insertion recess 122 may be formed above the second insertion recess 126. The diameter of the first insertion recess 122 can be the same as the outer diameter of the projecting system 170 that is inserted therein, so that the projecting system 170 can move only along the lengthwise direction within the first insertion recess 122. A first through-hole 125 may be formed in the rear of the first insertion recess 122, so that the first through-hole 125 may place the first insertion recess 122 in communication with the base 150. As such, the light emitted from the light source (not shown), which may be located in the base 150, may pass through the first through-hole 125 and subsequently enter the projecting system 170.

In one side of the first insertion recess 122, there may be a first slot 124 formed along a lengthwise direction. Here, the lengthwise direction is intended to mean the lengthwise direction of the camera body 120, i.e., the direction along which the light travels (as represented by arrows) in the illustration of FIG. 3. The first slot 124 may be formed penetrating through the one side of the camera body 120, and a securing member 136 can be movably inserted in the first slot 124. The securing member 136 can correspond to a screw.

In a corresponding manner to the first slot 124, there can be a securing indentation 172 formed in one side of the projecting system 170. The securing member 136 can be coupled to the securing indentation 172 by screw coupling or press fitting. After the projecting system 170 is moved along the lengthwise direction of the first insertion recess 122 and set in position, the securing member 136 can be inserted through the first slot 124 and coupled to the securing indentation 172, so that the projecting system 170 can be prevented from moving any further along the lengthwise direction. In cases where the securing member 136 corresponds to a screw, a thread can be formed in the inner diameter of the securing indentation 172 correspondingly.

Two securing indentations 172 can be formed symmetrically, on opposite sides, in the outer perimeter of the projecting system 170.

The second insertion recess 126 may be a recess having a circular cross section and may extend a particular length. The second insertion recess 126 can be formed shorter than the first insertion recess 122. However, the front ends of the first insertion recess 122 and second insertion recess 126 can be located at the same position along the lengthwise direction, as illustrated in FIG. 4. The diameter of the second insertion recess 126 can be the same as the outer diameter of imaging system 180 that is inserted therein, so that the imaging system 180 can move only along the lengthwise direction within the second insertion recess 126. Also, a second through-hole 129 may be formed in the rear of the second insertion recess 126, so that the second through-hole 129 may place the second insertion recess 126 in communication with the mirror-coupling space 131. As such, the light entering the imaging system 180 may pass through the second through-hole 129, be reflected off the mirror 144, and subsequently arrive at the sensor (no reference numeral) of the image board 140.

As illustrated in FIG. 5, the first insertion recess 122 and the second insertion recess 126 can be interconnected by a connection hole 118. The connection hole 118 may correspond to a rectangular hole formed along the lengthwise direction at the bottom of the first insertion recess 122 and the top of the second insertion recess 126. A portion of the imaging system 180 inserted in the second insertion recess 126 can be exposed by the connection hole 118, whereby the imaging system 180 can easily release heat.

At a front portion of the camera body 120, a coupling part 138 may be formed, which corresponds to an empty space. The periphery of the coupling part 138 may form a part of the exterior of the camera body 120. The coupling part 138 may be open at its front and may communicate with the first insertion recess 122 and the second insertion recess 126 at its rear. The cross section of the coupling part 138 can be shaped similar to an ellipse, as illustrated in FIG. 6. A portion of the imaging system 180 can be located in the coupling part 138, as illustrated in FIG. 3.

At the rear of the second insertion recess 126 in the camera body 120, a mirror-coupling space 131 may be provided. As illustrated in FIG. 3 and FIG. 4, the mirror-coupling space 131 may have a triangular cross section, and the mirror 144 may be disposed in an inclined orientation within the mirror-coupling space 131. A mirror-coupling face 130 formed within the mirror-coupling space 131 may be formed with a 45-degree angle with respect to the lengthwise direction, and the mirror 144 can be coupled to the front of the mirror-coupling face 130 by way of an adhesive, etc. A filling indentation 133 may be formed in each of the upper end and lower end of the mirror-coupling face 130, where the filling indentations 133 may be formed perpendicularly to the lengthwise direction of the camera body 120. An adhesive, etc., for coupling the mirror 144 to the mirror-coupling face 130 can be injected into the filling indentations 133. Thus, as separate filling indentations 133 are formed for coupling the mirror 144 onto the mirror-coupling face 130, it is possible to easily secure and position the mirror 144 even with the use of an adhesive.

The mirror-coupling space 131 can be structured to be open at one side. The user can use the open side to easily insert and couple the mirror 144 in the mirror-coupling space 131. The open side of the mirror-coupling space 131 can be covered by a triangularly shaped side cover 146.

The mirror-coupling space 131 may be in communication with the second insertion recess 126 by way of the second through-hole 129 and may be in communication with the exterior of the camera body 120 by way of a body opening 132. Light that has passed through the imaging system 180 inserted in the second insertion recess 126 can be reflected in an angle of 90 degrees by the mirror 144 provided within the mirror-coupling space 131 to arrive at the sensor provided on the sensor board 140.

The camera body 120 may include a flat sensor-coupling face 134 to which the sensor board 140 can be coupled. The sensor board 140 can be coupled to the sensor-coupling face 134 by way of bolts (not shown) or the like. The body opening 132 may be formed in the sensor-coupling face 134, and light that has entered the mirror-coupling space 131 can pass through the body opening 132 to arrive at the sensor.

Referring to FIG. 8, the projecting system 170 can have a generally cylindrical shape and can include multiple lenses (no reference numeral) and holders (no reference numeral).

An integrated optical engine 100 according to this embodiment provides the advantage that the projecting system 170 can be coupled easily by simply inserting the projecting system 170 into the first insertion recess 122. The position of the projecting system 170 within the camera body 120 with respect to the lengthwise direction is of particular importance, and with an integrated optical engine 100 according to this embodiment, it is possible to easily adjust the position of the projecting system 170 by using the first slot 124 and the securing indentation 172 and to easily maintain the set position by using the securing member 136.

Referring to FIG. 9, the imaging system 180 can have a generally cylindrical shape and can include multiple lenses and holders (no reference numeral). An integrated optical engine 100 according to this embodiment provides the advantage that the imaging system 180 can be coupled easily by simply inserting the imaging system 180 into the second insertion recess 126. The position of the imaging system 180 within the camera body 120 with respect to the lengthwise direction is also of particular importance, and with an integrated optical engine 100 according to this embodiment, it is possible to easily adjust the position of the imaging system 180 by using the second slot 128 and the securing indentation 182 and to easily maintain the set position by using the securing member 136.

The imaging system 180 can have one securing indentation 182 formed, or two securing indentation 182 formed symmetrically, in the outer perimeter of the imaging system 180. In cases where a thread is formed in the outer perimeter of the securing member 136, a thread can be formed in the inner perimeter of the securing indentation 182 as well.

The user can couple the securing member 136 to the securing indentation 172 of the projecting system 170 and then move the securing member 136 along the first slot 124 to thereby easily adjust the position of the projecting system 170 with respect to the lengthwise direction from outside the camera body 120. Similarly, the user can couple the securing member 136 to the imaging system 180 and then move the securing member 136 along the second slot 128 to thereby easily adjust the position of the imaging system 180 with respect to the lengthwise direction from outside the camera body 120.

After the positioning of the projecting system 170 and the imaging system 180 is complete, the user can easily secure the projecting system 170 and imaging system 180 at their positions by rotating the securing members 136 coupled respectively to the projecting system 170 and imaging system 180 such that the heads of the securing members 136 press against the camera body 120.

Although the optical engine 100 according to this embodiment is mentioned as being applicable to an intraoral scanner, the invention is not limited to specific usages. Thus, an optical engine 100 according to this embodiment can be used as an intravenous scanner, a facial scanner, or a testing scanner (e.g., for testing PCB's).

While the foregoing provides a description with reference to an embodiment of the present invention, it should be appreciated that a person having ordinary skill in the relevant field of art would be able to make various modifications and alterations to the present invention without departing from the spirit and scope of the present invention set forth in the scope of claims below.

What is claimed is:

1. An integrated optical engine comprising:
   a projecting system including a plurality of lenses for projecting light to an exterior;
   an imaging system including a plurality of lenses for receiving light from the exterior;
   a camera body having the projecting system and the imaging system coupled thereto; and
   a base having a light source coupled therein, the base formed from a material having a heat-emitting capability, the base coupled to a rear of the camera body,
   wherein a first insertion recess and a second insertion recess are formed in the camera body, the first insertion recess being configured to receive the projecting system inserted therein, the second insertion recess being configured to receive the imaging system inserted therein,
   wherein the first insertion recess extends along a lengthwise direction of the camera body and has a same diameter as an outer diameter of the projecting system such that the projecting system is movable within the first insertion recess along the lengthwise direction of the camera body, the second insertion recess extends along a lengthwise direction of the camera body and has a same diameter as an outer diameter of the imaging system such that the imaging system is movable within the second insertion recess along the lengthwise direction of the camera body,
   wherein a first slot is formed in a lengthwise direction in the first insertion recess, and a second slot is formed in a lengthwise direction in the second insertion recess,
   wherein the first and second insertion recesses are arranged in a vertical direction and the first insertion recess is formed above the second insertion recess,
   wherein the first insertion recess is longer than the second insertion recess,
   wherein front ends of the first and second insertion recesses are located at a same position along the lengthwise direction of the camera body,
   wherein the first insertion recess and the second insertion recess are connected with each other through a rectangular connection hole,
   wherein the rectangular connection hole is provided at a bottom of the first insertion recess and at a top of the second insertion recess.

2. The integrated optical engine of claim 1, wherein the projecting system inserted in the first insertion recess and the imaging system inserted in the second insertion recess are not exposed at an exterior of the camera body.

3. The integrated optical engine of claim 1, further comprising:
   a mirror configured to reflect light that has entered the imaging system; and
   a sensor board configured to receive the light that is reflected by the mirror.

4. The integrated optical engine of claim 3, wherein the camera body comprises a sensor-coupling face, the sensor-coupling face separated from the base and having the sensor board coupled to an exposed surface thereof, and
   a body opening is formed in the sensor-coupling face, the body opening permitting a transmission of the light that is reflected by the mirror.

5. The integrated optical engine of claim 3, wherein the camera body comprises a mirror-coupling face having the mirror coupled thereto, and a filling indentation is formed at an end portion of the mirror-coupling face.

6. The integrated optical engine of claim 4, wherein the camera body comprises a mirror-coupling space having the mirror positioned therein, the mirror-coupling space having a side thereof open, the mirror-coupling space positioned between the sensor-coupling face and the base.

7. The integrated optical engine of claim 1, wherein a securing member is coupled to each of the first slot and the second slot to secure positions of the imaging system and the projecting system with respect to the lengthwise direction of the camera body.

8. The integrated optical engine of claim 7, wherein a securing indentation is formed in a side of each of the projecting system and the imaging system, the securing indentation configured to receive the securing member coupled thereto.

\* \* \* \* \*